United States Patent [19]

Tobin

[11] Patent Number: 5,020,088
[45] Date of Patent: May 28, 1991

[54] TISSUE SAMPLE LOCALIZER DEVICE AND METHOD

[76] Inventor: John A. Tobin, No. 3 E. Pleasant, St. Paul, Minn. 55127

[21] Appl. No.: 496,095

[22] Filed: Mar. 15, 1990

Related U.S. Application Data

[63] Continuation of Ser. No. 173,313, Mar. 25, 1988, abandoned.

[51] Int. Cl.⁵ .......................... H05G 1/28; H05G 1/00
[52] U.S. Cl. ..................................... 378/164; 378/208
[58] Field of Search .......................... 378/37, 162–164, 378/177, 180, 204, 210, 208; 128/653, 659, 664

[56] References Cited

U.S. PATENT DOCUMENTS

| | | | |
|---|---|---|---|
| 581,540 | 4/1897 | Dennis | 378/164 |
| 1,453,473 | 5/1923 | McKenna | 378/180 |
| 2,111,903 | 3/1938 | Rona | 378/180 |
| 2,192,887 | 3/1940 | Black | 378/164 |
| 2,344,823 | 3/1944 | Landis et al. | 378/164 |
| 3,111,582 | 11/1963 | Levi | 378/164 |
| 4,259,585 | 3/1981 | Novak et al. | 378/37 |
| 4,563,768 | 1/1986 | Read et al. | 378/164 |
| 4,691,333 | 9/1987 | Gabriele et al. | 378/37 |
| 4,767,928 | 8/1988 | Nelson et al. | 128/664 |
| 4,837,795 | 6/1989 | Garrigus | 378/164 |

FOREIGN PATENT DOCUMENTS 0302993 1/1918 Fed. Rep. of Germany ...... 378/164

OTHER PUBLICATIONS

"Refinements in Dignostic X-Ray Technics With the Use of Wire Grids" by Fixott et al. Jour. of the Amer. Dental Assoc. vol. 78 No. 1 Jan. 1969.
Radiology, Nov. 1987, vol. 165 (P.) Supplement, p. 173, No. 474.

Primary Examiner—Craig E. Church
Attorney, Agent, or Firm—Merchant, Gould, Smith, Edell, Welter & Schmidt

[57] ABSTRACT

A tissue sample localizer device comprises a tissue holder having a target region constructed and arranged for selective receipt of a tissue sample to be analyzed thereon. A reference grid defines a grid pattern suitable for formation of a grid pattern image on an image taken of the reference grid. Structure is provided so that the reference grid is operably positioned over the tissue holder target region so that the grid pattern image appears on an image taken of the target region.

12 Claims, 3 Drawing Sheets

TISSUE SAMPLE LOCALIZER DEVICE AND METHOD

This is a continuation of application Ser. No. 173,313, filed Mar. 25, 1988, now abandoned.

TECHNICAL FIELD OF THE INVENTION

The present invention relates generally to the field of radiology and more specifically to a device and method to more accurately and efficiently localize and reference resected tissue samples.

BACKGROUND OF THE INVENTION

Within the field of health care, there exists a need for accurate, efficient, and timely diagnosis of patient illnesses. Therefore, physical examinations which may allow detection of illnesses or developing health problems are quite important. However, even when health care providers are capable of detecting certain illnesses associated with a patient, the scope or severity of the illness may remain unknown.

In many instances, the detection of unhealthy tissue is delayed until such tissue presents complications. For example, in many forms of carcinomas, or cancers, the growth of undesired tissue remains undetected until secondary indications are noted by the patient. Generally, the earlier a diagnosis of carcinoma is made, then the better the chance of a positive outcome when dealing with that illness. An often preferred diagnostic method includes use of a tissue imaging device. Imaging techniques, such as X-ray photography, often provide indications of regions containing tumors, malignancies, masses, or other tissue anomalies.

Generally, when a tissue anomaly region has been detected, a health care provider accesses the region with surgical or other means. However, when surgical incisions are used to access potentially unhealthy tissue, extensive damage may result to otherwise healthy tissue. Furthermore, certain illnesses may require numerous incisions and tissue penetrations to arrive at the various suspect tissue masses. Even if one such unhealthy mass is detected, accessed, and removed, it remains a current practice to also remove a substantial amount of surrounding tissue in order to achieve a greater chance of a surgical cure. A similar problem exists when removal methods other than resection are used, such as hemostasis.

The procedures and methods of exploratory surgery and preventive surgery are often quite expensive. Medical providers who conduct certain surgical procedures are generally engaged in higher risk activities than many other medical providers, and therefore may incur significant other costs relating to surgical means of detecting and/or curing certain patient illnesses. These other risks and costs may include: occurrence of infection in points of incision; exuberant scarring, such as keyloids, in the incision regions; undesired damage to associated or adjacent tissue and organs; increased costs associated with recovery care; costs associated with related metabolic traumas; and insurance expenses.

The field of imaging analysis, including radiology, provides generally widely accepted initial alternatives to the surgical procedures noted above. A common method of imaging allows a patient to dispose that portion of his or her body in need of analysis between an emitter and a receptor portion of an imaging device. The device is activated to generate an emission of an energy form, such as sound, light, or radiographic waves, into and/or through the body portion being tested, thereby producing an image of the body portion in the receptor section of the device. Analysis of the image generated then provides diagnostic aids in the detection and pursuit of any unhealthy tissue. Unfortunately, such a technique often includes inaccuracies and inefficiencies. The size, width, density, or orientation of the exposed body portion may result in adverse imaging. Depending on the organ region being imaged, it is not uncommon to have images which include excessive shadowing, inarticulate detail, and even complete masking of various tissue.

The medical field has responded to these known problems affecting imaging methods of tissue analysis in several ways. One response includes taking multiple X-ray prints of a tissue region at various angles, so as to overcome shadowing and/or the physical blockage provided by organs, etc. This approach may result in unnecessary cycling and utilization of imaging equipment, waste of material, and inefficient use of trained personnel. Another method of tissue localization is exploratory surgery of the nature and disadvantages described hereinabove.

Yet another tissue localization method involves a relatively non-invasive removal of a sample portion of a suspect tissue region. This is accomplished through such means as a needle device having a hollow core into which a tissue specimen may be drawn and thereby removed from the patient. The tissue specimen may then be analyzed under a microscope or with other laboratory techniques such as radiographic analysis, X-ray photography, and the like. Although such means of extracting a tissue sample from a patient may reduce the size of the initial surgical incision and therefore may generally reduce the risk of this surgical procedure, certain inefficiencies remain. For instance, it is not uncommon for analysis of a tissue sample, using prior techniques, to require a long period of time. Such a long time period may often result in the patient departing the medical provider's office or surgical room prior to a completed analysis of the tissue specimen being made available. This results in significant inefficiencies if further tissue sampling is needed and/or the tissue analysis indicates that followon surgical procedures are necessary or recommended.

Frequently, the medical provider who removes a tissue specimen from a patient'3 s body provides that specimen to another medical provider for testing and analysis. For example, a surgeon may remove a breast tissue sample which is suspected of containing a carcinoma. The tissue sample may then be sent to a laboratory for analysis, probably by a radiologist and/or pathologist. After the analysis of the specimen is performed, the radiologist provides a report to the originating surgeon. Frequently, such reports highlight regions of the tissue sample which appear to be in need of further pathologic testing. In such cases, the tissue sample would then be provided to a pathology laboratory for further testing and analysis.

Many health care providers are not equipped with the requisite imaging devices, pathology laboratories, and trained personnel to accomplish the aforementioned tissue sample analysis. Therefore, tissue samples must leave the immediate control of the original medical provider and be transported to the appropriate location(s) for analysis. This process may result in considerable inefficiencies as well as risk of miscommunication as to the precise region of concern within a tissue sample. Also, miscommunication as to precise points in the tissue sample may occur in reporting or discussing the results of the analysis. A miscommunication or misunderstanding pertaining to this analysis results in a lengthening of the time from when the tissue sample was removed from the patient until the time when the appropriate medical provider receives the proper recommendations and information from other medical specialists.

What has been needed, therefore, has been a method to localize and reference tissue cells in an efficient and accurate manner.

What has been further needed has been a device which is readily operable for the localization and reference of tissue cells.

Other objects and advantages will become apparent from the following descriptions, taken in connection with the accompanying drawings, wherein are set forth by way of illustration and example certain embodiments of the present invention.

SUMMARY OF THE INVENTION

A device or arrangement is provided to facilitate the detection and localization of tissue sample regions which may be in need of testing or removal. More specifically, the device is operable to assist in the analysis of tissue specimens, such as tissue removed from a human breast. In particular, the device is selectively operable to support a tissue specimen and to provide a means for referencing specific points or locations on or within the tissue sample. The device is particularly well suited for use in association with tissue specimens requiring relatively rapid analysis. For example, a tissue mass which may include a malignancy or carcinoma that should be promptly analyzed.

Devices according to the present invention include means for supporting a tissue specimen, and means for referencing portions of a tissue specimen for placement of locator needles. Preferably a supporting means includes a tissue holder having a target region within which tissue specimens are selectively placed for analysis. It will be understood from the detailed description that such a target region could be located at virtually any location on a tissue holder which would also provide exposure to an imaging means.

A tissue sample localizer device according to the present invention also includes a reference grid which defines a grid pattern suitable for formation of a grid pattern image on an image taken of the reference grid. Positioning means are provided which operably position the reference grid relative to the tissue holder, such that the grid pattern image appears on an image taken of the tissue holder region. Thus, a tissue sample located in a tissue holder target region can be imaged, along with an associated reference grid, so that the image includes means for identifying points on the tissue sample intended for further testing.

A tissue holder target region should preferably be provided which is substantially transparent to an imaging medium. A preferred target region is located approximately in the center of a tissue holder in order to provide surrounding work space. It will be further understood that a tissue holder need only have means for supporting a tissue specimen within the path of an imaging device and may accordingly be comprised of varied materials and be of varied shape.

A referencing means in accordance with the present invention, preferably comprises a member which is constructed and arranged as a referencing system in relation to a tissue sample and in relation to an image of the tissue sample. Preferably, a reference system provides identification of points within a grid; with the grid oriented in relation to a tissue specimen so as to facilitate accurate detection of points within the tissue specimen. The referencing means includes a reference grid having a plurality of grid sections. Those grid sections may intersect and be arranged to form any shape. Preferably a generally square grid is formed comprised of numerous grid sections which may be easily identified by use of X-Y referencing means. Various grid shapes and/or referencing means may be used such as polar coordinate, circular-radian, or others.

A reference grid should be constructed of material having sufficient density to form an image of the grid on an imaged print. The projection of a grid outline onto an imaged print, such as an X-ray print, provides an efficient means for referencing points on that image. This facilitates accurate locating and referencing of specified points on a tissue specimen, while viewing an image or print of the tissue specimen. It may also provide precise referencing means for points on the actual tissue sample while the sample is in place on a tissue holder. Such in-place precision referencing means may include a reference grid which has apertures therein that allow extension of locator needles therethrough. The needles may be lodged into a tissue sample on the tissue holder to mark desired points with great accuracy. The reference grid sections may then be used to support the inserted needles. A reference means in accordance with this invention may also be constructed integral to a tissue holder target region.

Preferably, X-ray photography is used to image the reference grid and tissue sample. X-ray imaging could be provided in accordance with this invention by arranging a reference grid member in association with a tissue holder target region so that a tissue sample being supported in that target region is exposed in line with the reference grid. Imaging of the reference grid and the tissue sample creates a print which readily provides accurate reference means to various parts of the tissue sample. The tissue holder target region used with this device should be substantially transparent to the particular imaging source utilized. This transparency provides improved clarity of the tissue specimen and reference grid when imaged. It is possible, however, that a tissue holder target region could be comprised of a filtered medium or other material for the production of a desired background effect in relation to the tissue specimen being imaged.

Preferred devices according to the present invention include a tissue holder which is comprised of a plate with an aperture located therein. An aperture allows for selective and removable placement of a laboratory type slide made of glass, plastic, or other generally transparent material onto a tissue holder. The slide would be supported by the tissue holder, positioned over the aperture, and would provide direct contact and support for the tissue specimen. One advantage of a plate with an aperture is the reduced need for frequent sterilization procedures due to the tissue sample being positioned on a removable and/or disposable material over a target region, rather than in direct contact with the tissue holder. Further advantages of this construction include a reduction in fogging or condensation effect which may degrade the accuracy of conventional imaging methods, and improved temperature control of tissue specimens. For example, a frozen or temperature regulated tissue specimen may be mounted without substantial heat sinking effect which may otherwise occur if the tissue specimen is placed directly on a holder of a tissue sample localizer device which is significantly warmer or colder than the specimen.

A further means of limiting such fogging, condensation, temperature effects, and undesired contact of a tissue specimen with a tissue sample localizer device or an imaging device includes support means for a tissue holder. Tissue holder support means may include at least one leg mechanism. Several leg mechanisms could also be attached to a tissue holder in order to provide distancing between a tissue holder and a mounting surface of an imaging device. These legs or distancing means may be adjusted to vary the distance between a tissue holder and an imaging device mounting surface depending on the requirements of the particular imaging device, tissue specimen, or other considerations.

Preferred devices according to the present invention include a reference grid constructed of wire material which appears as a grid outline on an X-ray image. Materials other than metallic wire are also acceptable, provided the construction affords a suitable capability for imaging.

A reference grid may be comprised of a plate with an aperture located therein and a grid material placed across the aperture. Another possible structure of a reference grid includes a substantially transparent plate with a grid material embedded therein. A substantially transparent material allows a sufficient amount of the imaging source or imaging rays to penetrate the material sufficient to cause an image to be created. Even a reference grid comprised of a solid material without apertures therein could be used. However, if such a reference grid were constructed of a material which was impenetrable by minor puncture force, then it would generally not be as preferable as other reference grids with apertures included. A reference grid constructed of a thin, substantially transparent and readily penetrable material could provide some of the advantages desired when used in conjunction with other portions of this invention. For example, a clear poly wrap with metalized grids therein may be acceptable.

In a preferred device, the tissue holder may also be arranged to function as a mounting base for a leg mounted reference grid plate. Preferably, the reference grid plate includes at least one aperture with a wire grid positioned across the aperture. Leg mounting means allow the reference grid plate to be positioned in alignment with the tissue holder target region.

Further means for precision referencing include a pattern or arrangement of reference grid coordinate labels which may be placed in association with the reference grid. These coordinates are constructed to be visible on images of the tissue specimen and the reference grid. These precision coordinates may be employed by a plastic template placed on the reference grid; the template containing metalized coordinate figures.

Means are also provided to align a preferred tissue sample localizer device in relation to a particular imaging machine. For example, one alignment means is a conventional hook and loop attachment system (such as Velcro ®) which allows for placing the device in consistent positionable relationship with the imaging machine.

Although alignment means may not always be desirable, such a feature reduces referencing problems which may otherwise waste time in evaluation of the images produced. Other tissue holder and reference grid alignment means include: alignment notches; leg mechanism grooves; and the like. A preferred embodiment of the present invention includes a reference grid which is aligned and mounted in association with a tissue holder so as to provide a structure or device which provides accurate detection and localization of tissue samples.

In accordance with the present invention, there is also disclosed a method for detecting and localizing tissue samples. The preferred method includes a tissue sample localizer device as described above.

This method of detecting and localizing tissue samples includes placing a tissue sample which is in need of testing into a tissue holder target region. Then, a reference grid is positioned in association with the target region. Both the tissue sample and reference grid are imaged with an imaging device suitable to provide medically useful information pertinent to the tissue health or configuration. Analysis of the resulting image permits locations on the tissue and the tissue image to be established by use of the reference grid image and the reference grid. Articulation of precise points on the image is enhanced by precision referencing means in the form of coordinates which are preferably displayed on the image. If further referencing is desired, locator needles may be inserted through the reference grid and placed in the tissue sample itself to define specific points in the tissue sample. The individual user, such as a medical provider, could remove the reference grid in a direction that would allow the locator needles to remain intact in the tissue sample. By removing the reference grid from association with the tissue holder, the user may then remove the tissue sample to a location for further testing with the precision locator needles intact therein. This method therefore teaches greater efficiency and accuracy in the detection and localization of tissue samples.

The efficient method described herein is of particular application during surgical or other procedures in which overall risk may be reduced by more efficient testing. Improved efficiencies resulting from application of this invention allow for breast tissue resection, testing, analysis, and reporting with minimal delay. In such cases, a patient and a medical provider may even determine a follow-up protocol prior to completion of an initial office visit.

The drawings constitute a part of this specification and include exemplary embodiments of the present invention, while illustrating various objects and features thereof. It will be understood that in some instances relative material thicknesses and relative component sizes may be shown exaggerated, to facilitate an understanding of the invention.

BRIEF DESCRIPTION OF THE DRAWINGS

While the specification concludes with claims particularly pointing out and distinctly claiming the subject matter as forming the present invention, it is believed that the invention will be better understood from the following description taken in connection with the accompanying drawings in which.

DETAILED DESCRIPTION WITH PREFERRED EMBODIMENTS

As required, detailed embodiments of the present invention are disclosed herein. It is to be understood, however, that the disclosed embodiments are merely exemplary of the invention, which may be embodied in various forms. Therefore, specific structural and functional details disclosed herein are not to be interpreted as limiting, but rather as a basis for the claims and as a representative basis for teaching one skilled in the art to variously employ the present invention in virtually any appropriately detailed system or structure.

Figure 1:
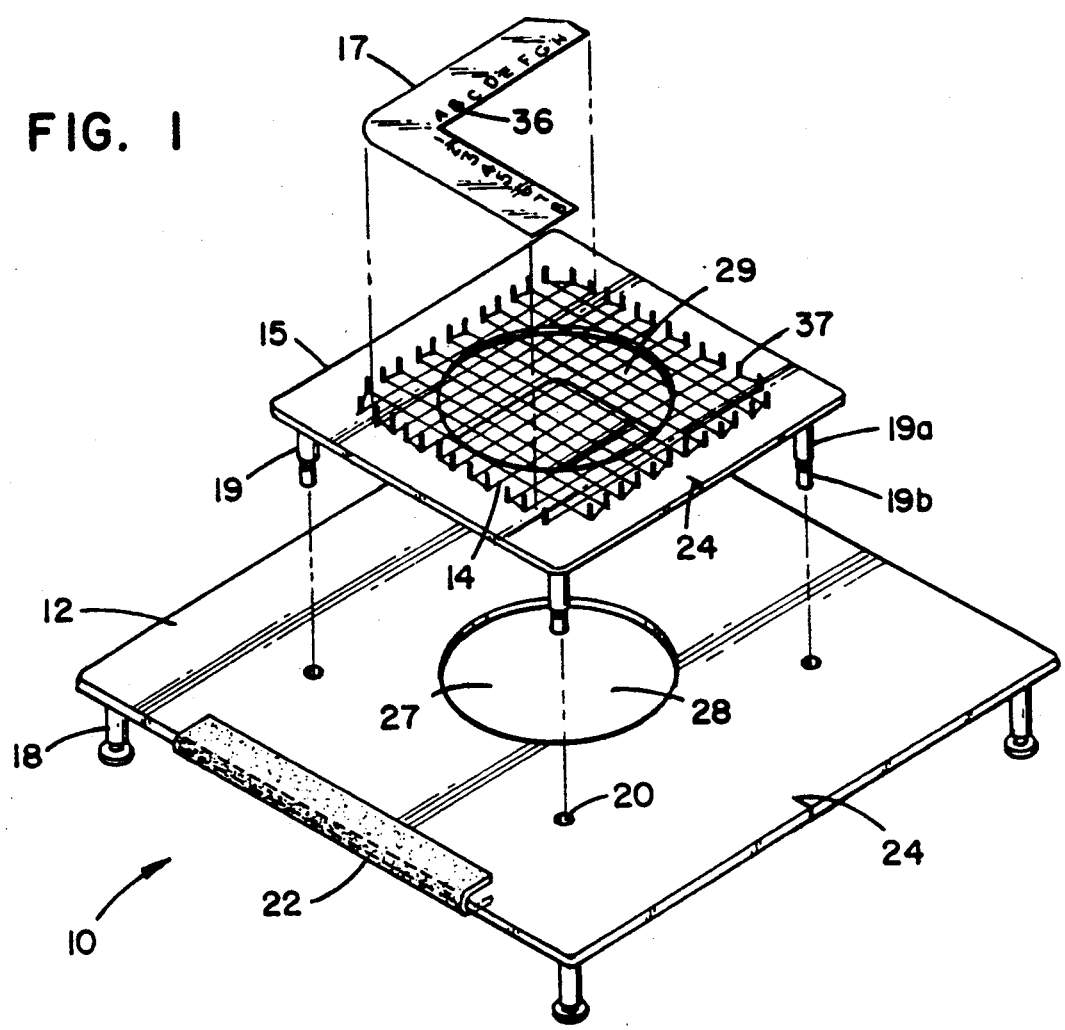
FIG. 1 is an exploded perspective view of a device according to the present invention, the device illustrated having a tissue support plate, a reference grid plate, and a reference template.

Referring to FIGS. 1-6, the reference numeral 10 generally designates a device according to the present invention. In FIG. 1, a tissue sample localizer device 10 is illustrated including: a tissue holder preferably in the form of a tissue support plate 12; a reference grid 14 preferably in the form of a grid plate 15; and, grid reference character member in the form of a template 17. In a preferred embodiment, support means 18 is provided in association with tissue support plate 12 for positioning a specimen at a selected and convenient height above an X-ray table or other mechanism. Positioning means 19 is provided in association with grid plate 15 to operably position grid plate 15 relative to tissue holder support plate 12. Positioning means 19 includes leg members having a first end 19a positioned on reference grid 14 and a second end 19b positioned on tissue support plate 12. Grid plate positioning means 19 may be aligned with and positioned in mounting recesses or grooves 20 in tissue support plate 12. Reference grid 14 is rotationally adjustable relative to the tissue holder, or the tissue support plate 12.

Figure 2:
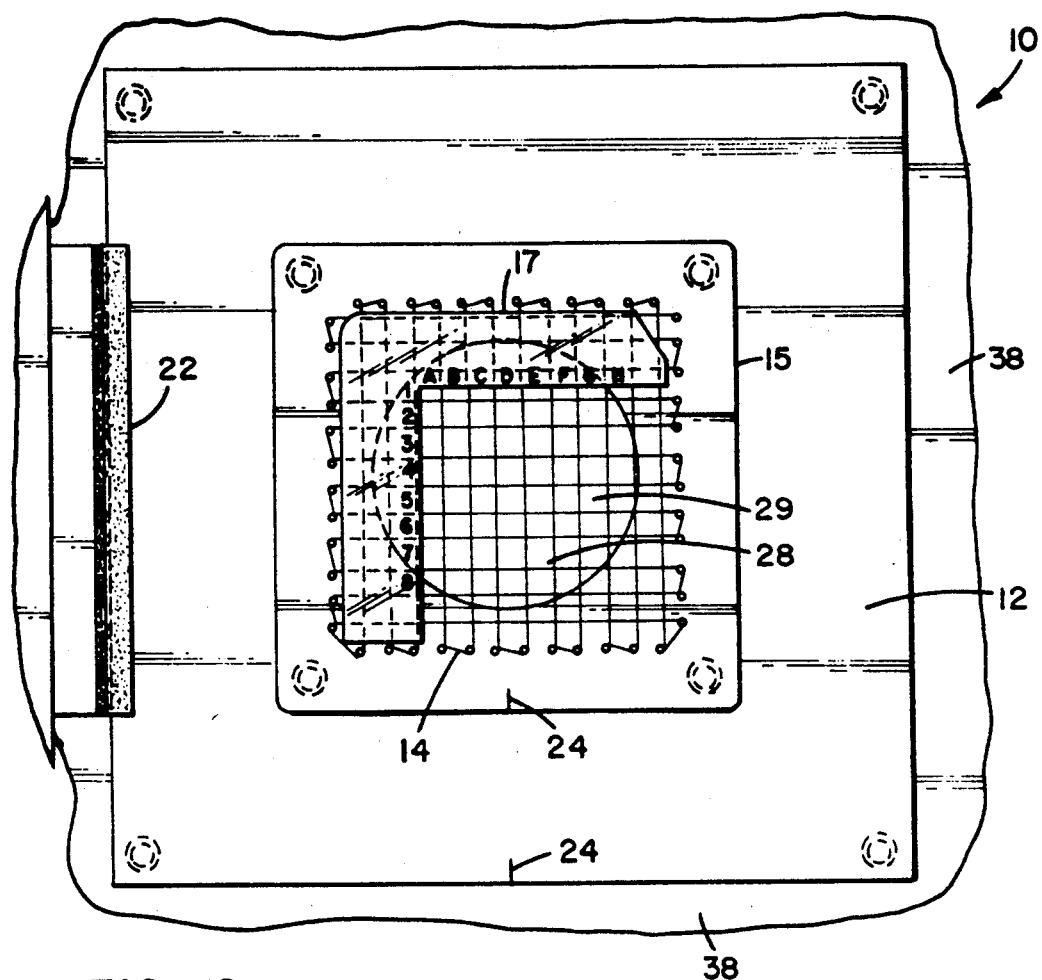
FIG. 2 is a top plan view of a tissue sample localizer device shown mounted on an X-ray table and showing an aligning means attaching the device to the X-ray table.

As shown in FIG. 1 and FIG. 2, tissue support plate 12 includes means for aligning support plate 12 with an X-ray table or other mechanism. For a preferred embodiment, a hook and loop anchoring means 22 is provided; thereby permitting attachment between tissue support plate 12 and an X-ray table or other mechanism. Referring to FIG. 1, tissue support plate 12 and grid plate 15 may also include alignment indicator indicia in the form of notches 24 located preferably in at least one side of tissue support plate 12 and grid plate 15. Alignment notches 24 generally provide alignment of grid plate 15 with tissue support plate 12.

As shown in FIG. 1, an aperture 27 defining a portion of a target region 28 located in tissue support plate 12 and an aperture 29 is located in grid plate 15. In a preferred embodiment, reference grid 14 is positioned across grid plate aperture 29. Reference grid 14 is preferably constructed of material with a density that is sufficient to provide an image of reference grid 14 on a radiographic print or other image; the image being preferably taken from above grid plate 15 facing in a generally downward direction through reference grid 14, grid plate aperture 29, and tissue support plate aperture 27. Preferably, reference grid 14 is constructed of metallic wire material which is sufficient to form an outline on imaged prints. A grid outline on an imaged print provides means for referencing and localizing a point on the print, and may be enhanced by use of labeling. Reference means, or labeling, may include a generally transparent template 17 with reference designations 36 thereon; the reference designations also being constructed of material sufficient to form an outline on an imaged print. In a preferred embodiment, wire grid 14 is positioned across grid plate aperture 29 by attachment to stanchions 37 in grid plate 15. Other attaching means may be used while still achieving certain advantages with device 10.

FIG. 2 illustrates a preferred construction of tissue sample localizer device 10 when viewed from above. This construction permits positioning of device 10 beneath an emitter portion of an imaging device, such as an X-ray machine. When positioned as in FIG. 2, tissue sample localizer device 10 allows an image or X-ray print to be taken from a perspective oriented generally downwardly through reference template 17, grid plate 15, grid plate aperture 29, and target region 28 in tissue support plate 12.

Figure 3:
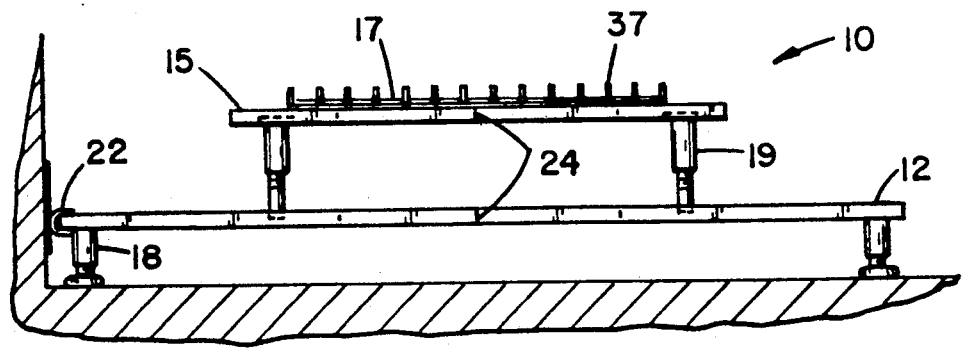
FIG. 3 is a side elevational view of a device depicted in FIG. 2.

As shown in FIG. 2, grid plate 15 is aligned on tissue support plate 12 by means of alignment notches 24. Also, as shown in FIG. 2 and FIG. 3, tissue support plate 12 is aligned on an imaging device support 38 by anchoring means 22 located on tissue support plate 12 and imaging device support 38. Various attaching and aligning means may include: a mark on the imaging table; a snap-on attaching means; or other well-known mechanisms.

FIG. 3 illustrates a side elevational view of a preferred embodiment of tissue sample localizer device 10 analogous to FIG. 2. As depicted, tissue support plate 12 may be elevated from imaging device support 38 to prevent shadowing, condensation effects, or for other reasons. This elevation is preferably achieved by tissue support plate support means 18. Support means 18 preferably comprise adjustable legs. Positioning means 19 for grid plate 15 are also provided. Positioning means 19 is preferably comprised of adjustable leg members which may be similar to support means 18.

Figure 4:
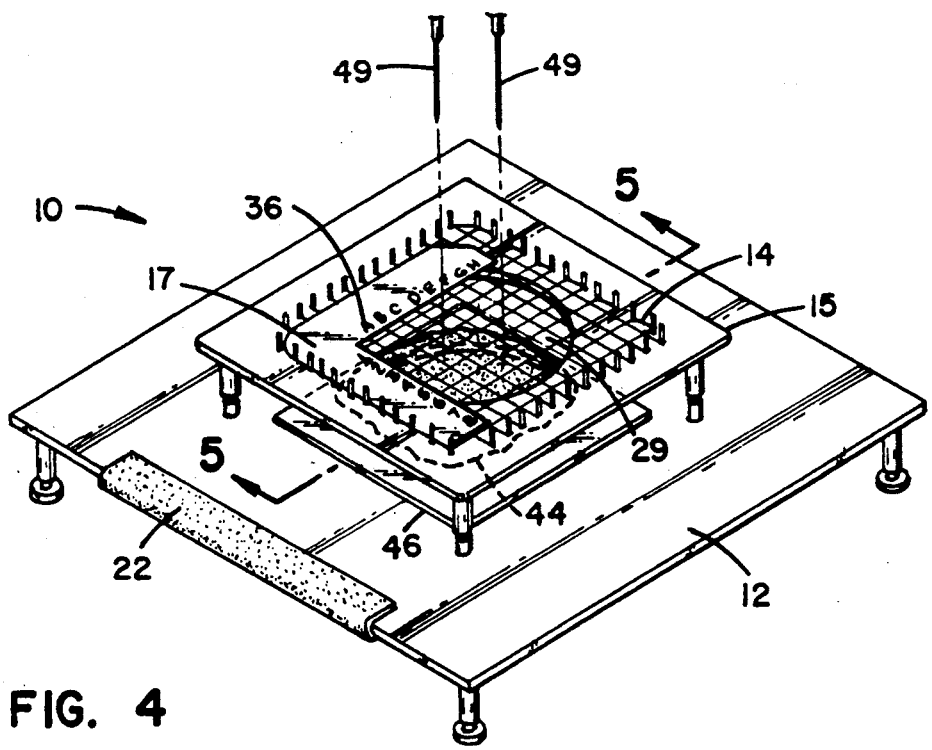
FIG. 4 is a perspective view of a tissue sample localizer device including a tissue sample mounted thereon; the device showing a preferred reference grid through which locator needles are positioned for insertion into the underlying tissue sample.

Referring to FIG. 4, a perspective view of a preferred tissue sample localizer 10 according to the present invention is shown. FIG. 4 includes a tissue sample 44 which is supported by a substantially transparent tissue mounting slide 46 positioned on tissue support plate 12 above tissue support plate aperture 27. Positioning of grid plate 15 relative to tissue support plate 12 allows grid plate aperture 29 and tissue support plate aperture 27 to be in vertical alignment; and in this embodiment permitting target region 28 to be aligned therebetween. Accordingly, when tissue sample 44 is positioned in target region 28 over tissue support plate aperture 27, and an image is taken from above grid plate 15 in a downward direction, the image of tissue sample 44 includes an image of reference grid 14 thereon.

After examination of the imaged print, a specialist may further localize regions of tissue sample 44 which may require pathologic testing, or for other reasons, by placement of locator needles 49 into tissue sample 44. This insertion is preferably accomplished by inserting a locator needle 49 through grid plate 15 and grid plate aperture 29 into tissue sample 44 at a desired location identified in relation to the image of reference grid plate 15. Multiple locator needles 49 may be used, as shown in FIG. 4. The reference designations 36 on reference template 17 are used to provide further localizing and referencing means.

Figure 5:
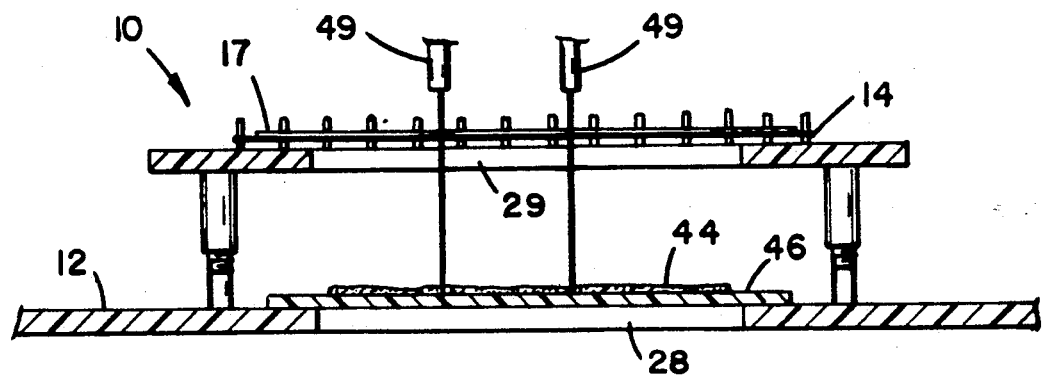
FIG. 5 is a cross-sectional view taken generally along line 5—5, FIG. 4, illustrating locator needles inserted into a tissue sample mounted on a plate that is placed on the tissue sample holder.

FIG. 5 illustrates a cut-away view generally along line 5—5, FIG. 4, of a preferred device 10 with a plurality of locator needles 49 inserted through grid plate 15, grid plate aperture 29, and extending into tissue sample 44. As illustrated, grid plate positioning means 19, in a preferred form, includes a plurality of adjustable support legs which position grid plate 15 at various distances or heights in relation to tissue support plate 12. Positioning means 19 may also be attached directly to reference grid 14 rather than to a grid plate. Adjustable positioning means 19 ensure proper spacing of grid plate 15 dependent on tissue sample variety, size of locator needles 49, or other factors.

As explained above, locator needles 49 provide great accuracy in localizing portions of tissue sample 44 in need of further testing. Therefore, once locator needles 49 are inserted into tissue sample 44, grid plate 15 may be lifted away from tissue sample 44 thereby allowing locator needles 49 to pass through the open grid sections of reference grid 14.

Figure 6:
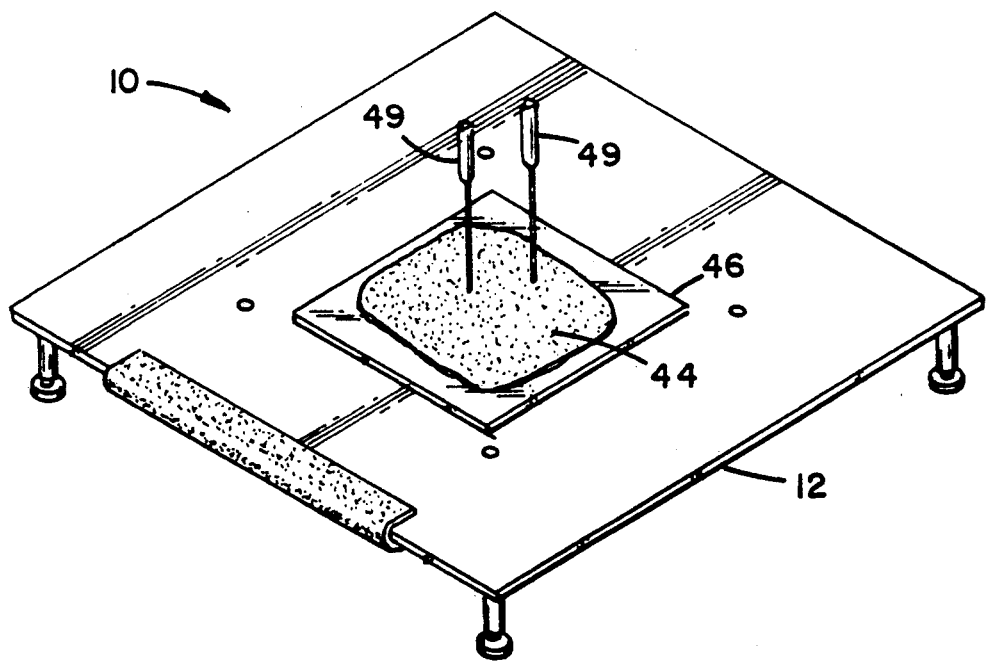
FIG. 6 is a perspective view generally analogous to FIG. 5, but with the reference grid plate and template removed.

After removal of grid plate 15 from device 10, as illustrated in FIG. 6, tissue sample 44 with locator needles 49 therein may be readily removed from tissue support plate 12 and made available for immediate testing or other use. Tissue sample localizing device 10 and its accompanying method thereby enhances the relative accuracy and speed with which tissue sample testing, interpretation, and localization may be accomplished. Such improvements may significantly reduce the health risks to patients; some of whom might otherwise require unnecessary surgical removal of healthy tissue; multiple invasive procedures; or other medical treatment.

The invention accordingly consists in the features of the construction, combinations of elements, arrangements of parts, and method of use which will be exemplified in the construction described above and of which the scope of the invention would be indicated in the following claims. It is to be understood that while certain embodiments of the present invention have been illustrated and described, the invention is not to be limited to the specific forms or arrangements of parts herein described and shown.

What is claimed is:

1. A tissue localizer device comprising:
   (a) a tissue holder having a target region constructed and arranged for selective receipt of a tissue sample to be analyzed thereon;
   (b) a reference grid, said reference grid defining a grid pattern suitable for formation of a grid pattern image on a radiographic image taken of said reference grid, said reference grid being permeable to passage of elongate needle-like members therethrough, said reference grid including a plate having an aperture therein; wherein a plurality of wire-like members are arranged across said reference grid plate aperture;
   (c) positioning means constructed and arranged to operably position said reference grid relative to said tissue holder target region such that said grid pattern image appears on a radiographic image taken of said target region.

2. A tissue sample localizer device according to claim 1 wherein said reference grid pattern is a rectangular pattern.

3. A tissue localizer device comprising:
   (a) a tissue holder having a target region constructed and arranged for selective receipt of a tissue sample to be analyzed thereon;
   (b) a reference grid, said reference grid defining a grid pattern suitable for formation of a grid pattern image on a radiographic image taken of said reference grid; said reference grid being rotationally adjustable relative to said tissue holder; and,
   (c) positioning means constructed and arranged to operably position said reference grid relative to said tissue holder so that said grid pattern image appears on a radiographic image taken of said target region, said positioning means including first and second alignment indicator indicia, said first alignment indicator indicia being located on said tissue holder, and said second alignment indicator indicia being located on said reference grid.

4. A tissue sample localizer device according to claim 3 including:
   (a) a grid reference character member operably positionable relative to said grid pattern to generate a reference character pattern in association with said grid pattern image, said grid reference character member being removable and replaceable.

5. A tissue sample localizer device according to claim 4 wherein said reference grid includes means for receipt of said grid reference character member thereon; and, said grid reference character member is positionable on said reference grid.

6. A tissue sample localizer device comprising:
   (a) a tissue holder having a target region constructed and arranged for selective receipt of a tissue sample to be analyzed thereon, said tissue holder target region including an aperture therein;
   (b) a reference grid; said reference grid defining a grid pattern suitable for formation of a grid pattern image on a radiographic image taken of said reference grid; said reference grid including:
      (i) a plate having an aperture therein;
      (ii) a plurality of wire-like members arranged across said reference grid plate aperture;
      (iii) said grid pattern being permeable to passage of elongate needle-like members therethrough;
   (c) a support mechanism constructed and arranged to support said tissue holder above a surface of a radiographic imaging device; and,
   (d) positioning means constructed and arranged to operably position said reference grid over said tissue holder target region in use, such that said grid pattern image appears on a radiographic image taken of said target region.

7. A tissue sample localizer device according to claim 6 including:
   (a) a removable and replaceable grid reference character member operably positionable relative to said grid pattern to generate a reference character pattern in association with said grid pattern image.

8. A tissue sample localizer device comprising:

(a) a tissue holder having a target region constructed and arranged for selective receipt of a tissue sample to be analyzed thereon; said tissue holder target region including an aperture therein;

(b) a reference grid; said reference grid defining a grid pattern suitable for formation of a grid pattern image on a radiographic image taken of said reference grid; said reference grid including:
   (i) a plate having an aperture therein;
   (ii) a plurality of wire-like members arranged across said references grid plate aperture;
   (iii) said grid pattern being permeable to passage of elongate needle-like members therethrough;

(c) a support mechanism constructed and arranged to support said tissue holder above a surface of a radiographic imaging device; and (d) positioning means constructed and arranged to operably position said reference grid over said tissue holder target region in use so that said grid pattern image appears on a radiographic image taken of said target region, said positioning means including a plurality of adjustable leg members operably positioned between said reference grid and said tissue holder; each of said leg members including a first end portion and a second end portion; said first end portion of each leg member being on said reference grid; and, said positioning means including recesses located within said tissue holder; each of said recesses being adapted for receipt therein of one each of said leg member second end portions.

9. An operable combination comprising:
(a) a tissue holder having a target region constructed and arranged for selective receipt of a tissue sample to be analyzed thereon; said tissue holder target region including an aperture therein;

(b) a reference grid; said reference grid defining a grid pattern suitable for formation of a grid pattern image on a radiographic image taken of said reference grid; said reference grid including:
   (i) a plate having an aperture therein;
   (ii) a plurality of wire-like members arranged across said reference grid plate aperture;
   (iii) said reference grid being permeable to passage of elongate needle-like members therethrough;

(c) a support mechanism constructed and arranged to support said tissue holder above a surface of a radiographic imaging device;

(d) positioning means constructed and arranged to operably position said reference grid relative to said tissue holder target region in use, such that said grid pattern image appears on a radiographic image taken of said target region; and, (e) a substantially transparent plate constructed and designed for operably holding a tissue sample relative to said tissue holder target region aperture so that when a radiographic image of said reference grid pattern is taken, said tissue sample is included in that radiographic image permitting locations on said tissue sample to be accurately referenced on said radiographic image.

10. A method for imaging a tissue sample, said method including the steps of:
(a) providing a tissue sample localizer device including:
   (i) a tissue holder having a target region constructed and arranged for selective receipt of a tissue sample to be analyzed thereon;
   (ii) a reference grid, said reference grid defining a grid pattern suitable for formation of a grid pattern image on a radiographic image taken of said reference grid, said reference grid being permeable to passage of elongate needle-like members therethrough, said reference grid including a plate having an aperture therein, wherein a plurality of wire-like members are arranged across said reference grid plate aperture;
   (iii) positioning means constructed and arranged to operably position said reference grid relative to said tissue holder, such that said grid pattern image appears on a radiographic image taken of said target region, said positioning means being constructed and arranged to operably support said reference grid over said tissue holder target region in use;

(b) orienting a tissue sample to be imaged on said target region;

(c) radiographically imaging said tissue sample located on said sample localizer device; and (d) inserting at least one locator needle through said reference grid into said tissue sample located in said tissue holder target region.

11. A method according to claim 10 including a step of removing said reference grid from relation with said tissue holder.

12. A tissue localizer device for radiographically localizing selected tissue abnormalities, comprising:
(a) a tissue holder constructed and arranged for receipt of a tissue sample removed from a patient, said tissue sample to be radiographically imaged and then pathologically analyzed whole remaining immobilized on said tissue holder; and (b) a reference grid comprising grid material constructed and arranged to define at least one aperture suitable for passage of at least one elongate needle-like member through said reference grid for insertion into the tissue sample; said grid material comprising grid sections suitable for formation of a grid pattern image on a radiographic image taken of said reference grid, said tissue holder, and the tissue sample; whereby said reference grid may then be removed without dislocating any needle-like member extending therethrough to permit subsequent pathological analysis of the radiographically imaged and localized tissue sample abnormalities, while the tissue sample remains in place on said tissue holder, so that each said elongate needle-like member may be inserted into the tissue sample and remain therein after removal of the reference grid.

* * * * *